(12) United States Patent
Li et al.

(10) Patent No.: US 9,891,184 B2
(45) Date of Patent: Feb. 13, 2018

(54) DITHIENYLPYRROLE-BASED BIOSENSORS AND METHODS FOR THEIR PREPARATION AND USE

(71) Applicant: Jiangnan University, Wuxi (CN)

(72) Inventors: Zaijun Li, Jiangsu (CN); Qianfang Xia, Jiangsu (CN); Xiulan Sun, Jiangsu (CN); Junkang Liu, Jiangsu (CN); Guangli Wang, Jiangsu (CN); Zhiguo Gu, Jiangsu (CN)

(73) Assignee: Jiangnan University, Wuxi (CN)

( * ) Notice: Subject to any disclaimer, the term of this patent is extended or adjusted under 35 U.S.C. 154(b) by 223 days.

(21) Appl. No.: 14/758,421

(22) PCT Filed: Dec. 31, 2012

(86) PCT No.: PCT/CN2012/088063
§ 371 (c)(1),
(2) Date: Jun. 29, 2015

(87) PCT Pub. No.: WO2014/101193
PCT Pub. Date: Jul. 3, 2014

(65) Prior Publication Data
US 2015/0346134 A1 Dec. 3, 2015

(51) Int. Cl.
| | | |
|---|---|---|
| *G01N 27/30* | (2006.01) | |
| *C08G 75/06* | (2006.01) | |
| *C08G 61/12* | (2006.01) | |
| *C07D 409/06* | (2006.01) | |
| *C09D 5/24* | (2006.01) | |
| *C09D 181/02* | (2006.01) | |
| *C25D 9/02* | (2006.01) | |
| *G01N 27/26* | (2006.01) | |
| *C07D 409/14* | (2006.01) | |
| *G01N 27/327* | (2006.01) | |
| *C08F 234/04* | (2006.01) | |
| *C08J 5/00* | (2006.01) | |
| *C08K 3/08* | (2006.01) | |
| *C08L 65/00* | (2006.01) | |

(52) U.S. Cl.
CPC ........... *G01N 27/30* (2013.01); *C07D 409/06* (2013.01); *C07D 409/14* (2013.01); *C08F 234/04* (2013.01); *C08G 75/06* (2013.01); *C08J 5/005* (2013.01); *C08K 3/08* (2013.01); *C09D 5/24* (2013.01); *C09D 181/02* (2013.01); *C25D 9/02* (2013.01); *G01N 27/26* (2013.01); *G01N 27/3277* (2013.01); *C08G 61/124* (2013.01); *C08G 61/126* (2013.01); *C08G 2261/148* (2013.01); *C08G 2261/1426* (2013.01); *C08G 2261/3221* (2013.01); *C08G 2261/3223* (2013.01); *C08G 2261/44* (2013.01); *C08G 2261/512* (2013.01); *C08G 2261/94* (2013.01); *C08J 2365/00* (2013.01); *C08L 65/00* (2013.01); *G01N 27/3278* (2013.01)

(58) Field of Classification Search
CPC .... G01N 27/30; C08G 61/124; C08G 61/126; C08G 75/06
See application file for complete search history.

(56) References Cited

U.S. PATENT DOCUMENTS

| | | |
|---|---|---|
| 4,886,625 A | 12/1989 | Albarella et al. |
| 5,210,217 A | 5/1993 | Albarella et al. |
| 2011/0162870 A1 | 7/2011 | Markovich et al. |

FOREIGN PATENT DOCUMENTS

| | | | |
|---|---|---|---|
| CN | 102520038 A | 6/2012 | |
| CN | 1025200038 A | * 6/2012 | ........... G01N 27/327 |

OTHER PUBLICATIONS

Kim et al., Synthesis, electrochemical, and spectroelectrochemical properties of conductive poly-[2,5-di-(2-thienyl)-1H-pyrrole-1-(p-benzoic acid)], Synthetic Metals 160:413-418 (2010).
Cihaner et al., Processable electrochromic and fluorescent polymers based on N-substituted thienylpyrrole. Electrochimica Acta 54:665-670 (2008).
International Search Report and Written Opinion dated Sep. 18, 2013 for PCT Application No. PCT/CN2012/088063 dated Dec. 31, 2012.

\* cited by examiner

*Primary Examiner* — Joseph R Kosack
(74) *Attorney, Agent, or Firm* — Dorsey & Whitney LLP

(57) ABSTRACT

Dithienylpyrrole compounds, compositions containing dithienylpyrrole polymers, and methods for making the compounds and compositions are disclosed herein. The compositions containing dithienylpyrrole polymers, can for example, be used as conducting polymers in biosensors for detecting analytes in a sample.

22 Claims, No Drawings

DITHIENYLPYRROLE-BASED BIOSENSORS AND METHODS FOR THEIR PREPARATION AND USE

CROSS-REFERENCE TO RELATED APPLICATIONS

The present application is the U.S. National Phase filing under 35 U.S.C. § 371 of International Application No. PCT/CN2012/088063 entitled DITHIENYLPYRROLE-BASED BIOSENSORS AND METHODS FOR THEIR PREPARATION AND USE, filed Dec. 31, 2012. The content of this application is herein incorporated by reference in its entirety.

BACKGROUND

Field

The present disclosure relates to compositions and methods for detecting biological and chemical analytes.

Description of the Related Art

In biosensors, such as those used for detecting biological or chemical entities, bioreactive agents are generally fixed onto electrodes through physical adsorption or chemical bonding methods. The biosensors prepared by physical adsorption methods can be unstable since the physically adsorbed bioreactive molecules such as enzymes or antibodies can easily detach from the electrodes. Chemical bonding methods can produce biosensors that are more stable. For example, bioreactive molecules can be bonded to a conducting polymer film that coats the electrodes of the biosensors. Metals may be added to the conducting polymer film to increase the conductivity of the film. However, in coating such metal-polymer composite films onto the electrodes, particularly when the monomer compound forming the polymer film is a reducing agent, redox interactions between the monomer compound and a metal precursor solution in the coating mixture may deteriorate the function of the polymer film that is formed, and discourage attachment of the polymer film onto the electrodes. There is therefore a need for biosensors that are more stable, sensitive, and long-lasting, and improved methods of making the biosensors.

SUMMARY

Some embodiments disclosed herein provide a compound represented by Formula I:

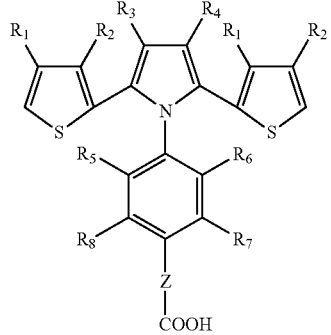

Formula I wherein:
Z is a bivalent hydrocarbyl group selected from the group consisting of alkylene, alkenylene and alkynylene;
$R_1$, $R_2$, $R_3$, and $R_4$ are each independently $C_1$-$C_6$ alkyl, $C_2$-$C_6$ alkylene, $C_2$-$C_6$ alkyne, hydrogen or halogen; and
$R_5$, $R_6$, $R_7$, and $R_8$ are each independently $C_1$-$C_{10}$ alkyl, $C_2$-$C_{10}$ alkylene, $C_1$-$C_{10}$ alkyne, hydrogen, or halogen.

In some embodiments, Z is $C_1$-$C_{10}$ alkylene, $C_2$-$C_{10}$ alkenylene, or $C_2$-$C_{10}$ alkynylene. In some embodiments, Z is a bivalent hydrocarbyl group selected from the group consisting of alkylene, alkenylene and alkynylene; and $R_1$, $R_2$, $R_3$, $R_4$, $R_5$, $R_6$, $R_7$, and $R_8$ are each independently hydrogen.

In some embodiments, Z is $C_1$-$C_{10}$ linear alkylene, $C_2$-$C_{10}$ linear alkenylene, or $C_2$-$C_8$ linear alkynylene.

In some embodiments, the compound is 2,5-di(2-thienyl)-1-pyrrol-1-(p-phenylacetic acid), 2,5-di(2-thienyl)-1-pyrrol-1-(p-phenylpropanoic acid, 2,5-di(2-thienyl)-1-pyrrol-1-(p-phenylpentanoic acid, 2,5-di(2-thienyl)-1-pyrrol-1-(p-phenylcaproic acid, or 2,5-di-(2-thienyl)-1H-pyrrole-1-(p-phenylbutanoic acid).

Some embodiments disclosed herein provide a composition comprising a dithienylpyrrole polymer, wherein the dithienylpyrrole polymer comprises at least two of the monomer units represented by Formula Ia:

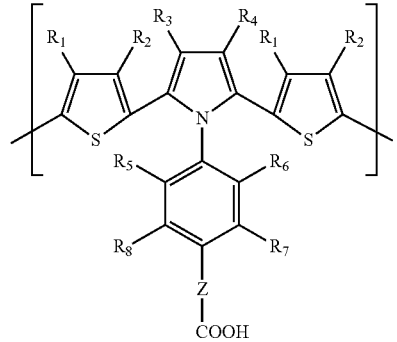

Formula Ia wherein:
Z is a bivalent hydrocarbyl group selected from the group consisting of alkylene, alkenylene and alkynylene;
$R_1$, $R_2$, $R_3$, and $R_4$ are each independently $C_1$-$C_6$ alkyl, $C_2$-$C_6$ alkylene, $C_2$-$C_6$ alkyne, hydrogen or halogen; and
$R_5$, $R_6$, $R_7$, and $R_8$ are each independently $C_1$-$C_{10}$ alkyl, $C_2$-$C_{10}$ alkylene, $C_1$-$C_{10}$ alkyne, hydrogen, or halogen.

In some embodiments, Z is $C_1$-$C_{10}$ alkylene, $C_2$-$C_{10}$ alkenylene, or $C_2$-$C_{10}$ alkynylene. In some embodiments, Z is a bivalent hydrocarbyl group selected from the group consisting of alkylene, alkenylene and alkynylene; and $R_1$, $R_2$, $R_3$, $R_4$, $R_5$, $R_6$, $R_7$, and $R_8$ are each independently hydrogen.

In some embodiments, Z is $C_1$-$C_{10}$ linear alkylene, $C_2$-$C_{10}$ linear alkenylene, or $C_2$-$C_8$ linear alkynylene.

In some embodiments, the monomer unit is a 2,5-di(2-thienyl)-1-pyrrol-1-(p-phenylacetic acid) monomer, a 2,5-di(2-thienyl)-1-pyrrole-1-(p-phenylpropanoic acid monomer, a 2,5-di(2-thienyl)-1-pyrrol-1-(p-phenylpentanoic acid monomer, a 2,5-di(2-thienyl)-1-pyrrol-1-(p-phenylcaproic acid monomer, or a 2,5-di-(2-thienyl)-1H-pyrrole-1-(p-phenylbutanoic acid) monomer.

In some embodiments, the composition further comprises metal nanostructures. In some embodiments, the weight ratio of the dithienylpyrrole polymer and the metal nanostructures is about 1:1 to about 3:1. In some embodiments, the metal nanostructures are selected from the group consisting of gold nanostructures, silver nanostructures, palladium nanostructures, copper nanostructures, nickel nanostructures, platinum nanostructures, rhodium nanostructures and ruthenium nanostructures, and a combination thereof. In some embodiments, the metal nanostructures comprise gold metal nanostructures. In some embodiments, the metal nanostructures are metal nanoparticles, metal nanowires, metal nanocube, metal nanorod, metal nanopyramid, metal nanotube, or a combination thereof In some embodiments, the composition is in the form of a film, a membrane, a foil, or a combination thereof.

Some embodiments provide a method for the preparation of a nanostructure film on a surface of a substrate, where the method includes: forming a composition comprising dithienylpyrrole monomers, at least one metal precursor, at least one organic solvent, at least one supporting electrolyte, and at least one amine compound; allowing metal nanostructures to form in the composition; and contacting the composition with a substrate under a condition effective to covalently bound two or more dithienylpyrrole monomers to form a dithienylpyrrole polymer and forming the nanostructure film on at least a portion of a surface of the substrate.

In some embodiments, the weight ratio of the dithienylpyrrole monomers, the metal precursor, the organic solvent, the supporting electrolyte, and the amine compound in the composition is about 1:1:83:10:5 to about 3:1:66:20:10.

In some embodiments, the dithienylpyrrole polymer comprises at least two of the monomer units represented by Formula Ia:

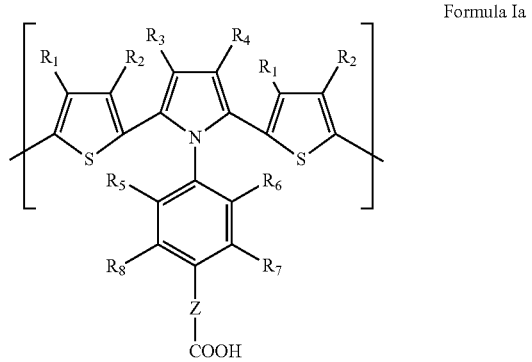

Formula Ia wherein:
Z is a bivalent hydrocarbyl group selected from the group consisting of alkylene, alkenylene and alkynylene;
$R_1$, $R_2$, $R_3$, and $R_4$ are each independently $C_1$-$C_6$ alkyl, $C_2$-$C_6$ alkylene, $C_2$-$C_6$ alkyne, hydrogen or halogen; and
$R_5$, $R_6$, $R_7$, and $R_8$ are each independently $C_1$-$C_{10}$ alkyl, $C_2$-$C_{10}$ alkylene, $C_1$-$C_{10}$ alkyne, hydrogen, or halogen.

In some embodiments, R is $C_1$-$C_8$ alkyl, $C_2$-$C_8$ alkylene, or $C_2$-$C_8$ alkyne.

In some embodiments, Z is a bivalent hydrocarbyl group selected from the group consisting of alkylene, alkenylene and alkynylene; and $R_1$, $R_2$, $R_3$, $R_4$, $R_5$, $R_6$, $R_7$, and $R_8$ are each independently hydrogen.

In some embodiments, Z is $C_1$-$C_{10}$ linear alkylene, $C_2$-$C_{10}$ linear alkenylene, or $C_2$-$C_8$ linear alkynylene.

In some embodiments, the monomer unit is a 2,5-di(2-thienyl)-1-pyrrol-1-(p-phenylacetic acid) monomer, a 2,5-di(2-thienyl)-1-pyrrol-1-(p-phenylpropanoic acid monomer, a 2,5-di(2-thienyl)-1-pyrrol-1-(p-phenylpentanoic acid monomer, a 2,5-di(2-thienyl)-1-pyrrol-1-(p-phenylcaproic acid monomer, or a 2, 5-di-(2-thienyl)-1H-pyrrole-1-(p-phenylbutanoic acid) monomer.

In some embodiments, the at least one metal precursor is selected from the group consisting of gold metal precursors, silver gold precursors, palladium metal precursors, copper metal precursors, nickel metal precursors, platinum metal precursors, rhodium nanostructures, ruthenium nanostructures, and a combination thereof. In some embodiments, the at least one metal precursor is a gold metal precursor. In some embodiments, the at least one metal precursor is $HAuCl_4$, $AgNO_3$ or a combination thereof. In some embodiments, the metal nanostructures are metal nanoparticles, metal nanowires, metal nanocube, metal nanorod, metal nanopyramid, metal nanotube, or a combination thereof.

In some embodiments, the at least one organic solvent is selected from the group consisting of n-hexane, chloroform, dichloromethane, n-heptane, carbon tetrachloride, and a mixture thereof.

In some embodiments, the at least one supporting electrolyte is a compound represented by Formula II: $(Y)_4N^- ClO4^{31}$, wherein Y is a $C_1$-$C_{30}$ alkyl, $C_1$-$C_{30}$ alkylene, $C_1$-$C_{30}$ alkyne, or an aromatic hydrocarbon group. In some embodiments, Y is a $C_1$-$C_4$ linear alkyl. In some embodiments, the at least one supporting electrolyte is selected from the group consisting of tetrabutylammonium perchlorate or tetrapropylammonium perchlorate, tetramethylammonium perchlorate, tetraamylammonium perchlorate, tetramethylammonium acetate, hexadecyltrimethylammonium acetate, hexadecyltrimethylammonium perchlorate, and a combination thereof.

In some embodiments, the at least one amine compound is a compound represented by Formula III:

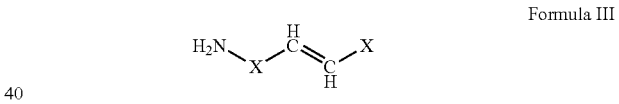

Formula III wherein X is a $C_6$-$C_{10}$ alkyl.

In some embodiments, the at least one amine compound is selected from the group consisting of oleylamine, 7-tetradecenylamine, 8-hexadecenylamine, and 11-docosenylamine. In some embodiments, the at least one amine compound is oleylamine.

In some embodiments, the substrate is an electrode. In some embodiments, the electrode is a glassy carbon electrode or a gold electrode.

In some embodiments, the forming the composition comprises stirring the composition at a temperature of about 45° C. to about 60° C. for about 10 hours to about 48 hours. In some embodiments, forming the composition further comprises maintaining the stirred composition at about room temperature for about 48 hours to about 72 hours.

In some embodiments, contacting the composition with the substrate comprises cyclic voltammetry scanning.

In some embodiments, the cyclic voltammetry scanning is performed at a voltage of about 0 V to about 1 V. In some embodiments, the cyclic voltammetry scanning is performed at a scanning rate of about 10 mV/s to about 500 mV/s.

Some embodiments provide a biosensor, where the biosensor includes: a working electrode configured to immobilize a bioreactive material, wherein the bioreactive material is reactive with a target material, wherein the working electrode comprises a dithienylpyrrole polymer and metal nanostructures, wherein the dithienylpyrrole polymer comprises at least two of the monomer units represented by Formula Ia:

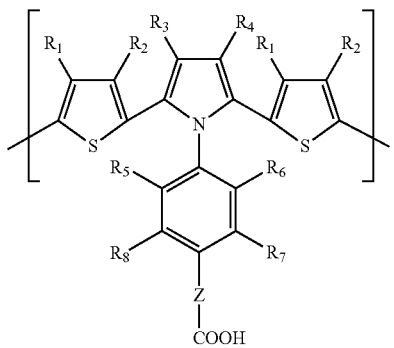

Formula Ia wherein:

Z is a bivalent hydrocarbyl group selected from the group consisting of alkylene, alkenylene and alkynylene;

$R_1$, $R_2$, $R_3$, and $R_4$ are each independently $C_1$-$C_6$ alkyl, $C_2$-$C_6$ alkylene, $C_2$-$C_6$ alkyne, hydrogen or halogen; and $R_5$, $R_6$, $R_7$, and $R_8$ are each independently $C_1$-$C_{10}$ alkyl, $C_2$-$C_{10}$ alkylene, $C_1$-$C_{10}$ alkyne, hydrogen, or halogen.

In some embodiments, the biosensor further comprises a reference electrode.

In some embodiments, the bioreactive material is reactive specifically with the target material. In some embodiments, the bioreactive material is selected from the group consisting of enzymes, antibodies, nucleic acids, peptides, peptide nucleic acids (PNA), aptamers, and a combination thereof.

In some embodiments, the metal nanostructures are selected from the group consisting of gold nanostructures, silver nanostructures, palladium nanostructures, copper nanostructures, nickel nanostructures, platinum nanostructures, and a combination thereof. In some embodiments, the metal nanostructures are in the form of metal nanoparticles, metal nanowires, metal nanocube, metal nanorod, metal nanopyramid, metal nanotube, or a combination thereof.

Some embodiments provide a method for detecting an analyte in a sample, where the method includes: providing a sample suspected of containing the analyte; contacting the sample with a biosensor, wherein the biosensor comprises a reference electrode and a working electrode configured to immobilize a bioreactive material, wherein the bioreactive material is reactive with the analyte, wherein the working electrode comprises a dithienylpyrrole polymer and metal nanostructures, wherein the dithienylpyrrole polymer comprises at least two of the monomer units represented by Formula Ia:

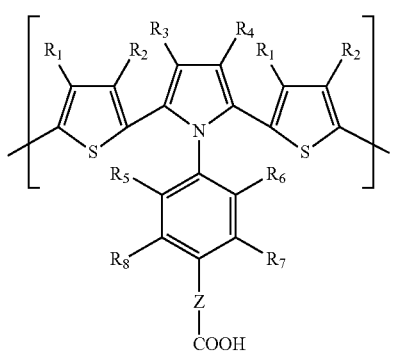

Formula Ia wherein:

Z is a bivalent hydrocarbyl group selected from the group consisting of alkylene, alkenylene and alkynylene;

$R_1$, $R_2$, $R_3$, and $R_4$ are each independently $C_1$-$C_6$ alkyl, $C_2$-$C_6$ alkylene, $C_2$-$C_6$ alkyne, hydrogen or halogen; and $R_5$, $R_6$, $R_7$, and $R_8$ are each independently $C_1$-$C_{10}$ alkyl, $C_2$-$C_{10}$ alkylene, $C_1$-$C_{10}$ alkyne, hydrogen, or halogen.

In some embodiments, the bioreactive material is selected from enzymes, antibodies, nucleic acids, peptides, peptide nucleic acids (PNA), aptamers, or a combination thereof. In some embodiments, the bioreactive material is an enzyme or antibody.

In some embodiments, the concentration of the analyte in the sample is about $10^{-3}$ mol/L to about $10^{-17}$ mol/L. In some embodiments, the concentration of the analyte in the sample is about $10^{-6}$ mol/L to about $10^{-17}$ mol/L. In some embodiments, the concentration of the analyte in the sample is not more than $10^{-9}$ mol/L.

In some embodiments, the analyte is selected from the group consisting of pesticides, small molecule compounds, proteins, hydrogen peroxide, pathogenic microorganisms, bacterial toxins, fungal toxins, viral toxins, and a combination thereof Some embodiments provide a method for the preparation of a compound represented by Formula I, where the method includes:

(1) contacting an optionally substituted thiophene

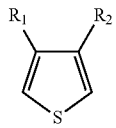

with a succinyl chloride

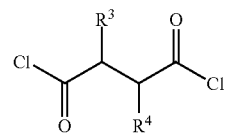

to obtain a first intermediate

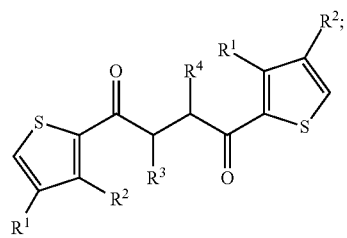

(2) contacting the first intermediate

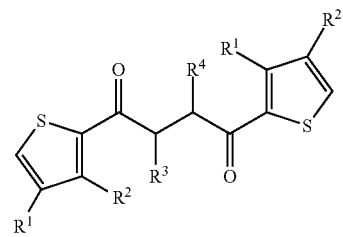

with a cyanoaniline

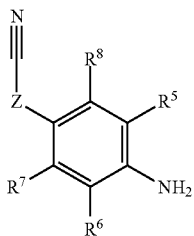

to obtain a second intermediate

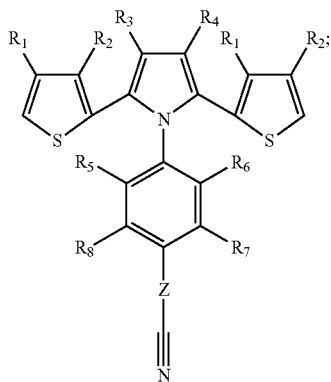

(3) hydrolyzing the nitrile group of the second intermediate

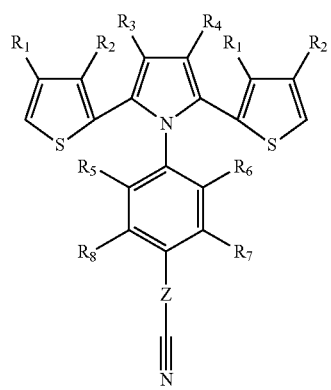

to obtain the compound of Formula I

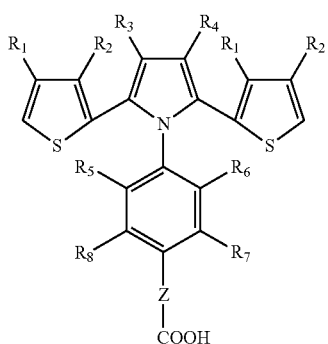

Formula I wherein:
Z is a bivalent hydrocarbyl group selected from the group consisting of alkylene, alkenylene and alkynylene;
$R_1$, $R_2$, $R_3$, and $R_4$ are each independently $C_1$-$C_6$ alkyl, $C_2$-$C_6$ alkylene, $C_2$-$C_6$ alkyne, hydrogen or halogen; and
$R_5$, $R_6$, $R_7$, and $R_8$ are each independently $C_1$-$C_{10}$ alkyl, $C_2$-$C_{10}$ alkylene, $C_1$-$C_{10}$ alkyne, hydrogen, or halogen.

In some embodiments, the optionally substituted thiophene

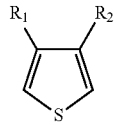

reacts with the succinyl chloride

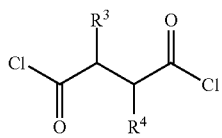

in the presence of aluminium trichloride. In some embodiments, the optionally substituted thiophene

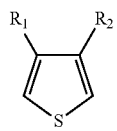

reacts with the optionally substituted succinyl chloride

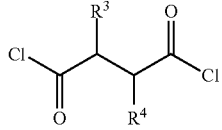

in the presence of at least one organic solvent.

In some embodiments, the at least one organic solvent is selected from the group consisting of dichloromethane, n-hexane, n-heptane, carbon tetrachloride, and a mixture thereof.

In some embodiments, the first intermediate

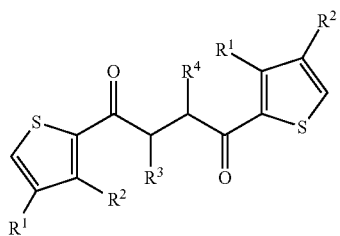

reacts with the cyanoaniline

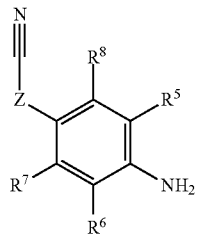

in the presence of an acid catalyst.

In some embodiments, the acid catalyst is p-toluenesulfonic acid or naphthalene sulfonic acid.

In some embodiments, the compound of Formula I is obtained from the second intermediate

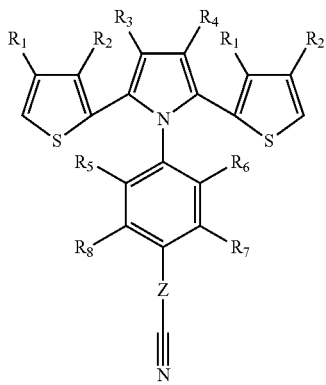

by alkaline hydrolysis.

In some embodiments, the alkaline hydrolysis is carried out in a mixture of potassium hydroxide aqueous solution and an organic solvent under reflux.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described hereincan be arranged, substituted, combined, and designed in a wide variety of different configurations, all of which are explicitly contemplated and make part of this disclosure.

Disclosed herein are dithienylpyrrole compounds represented by Formula I:

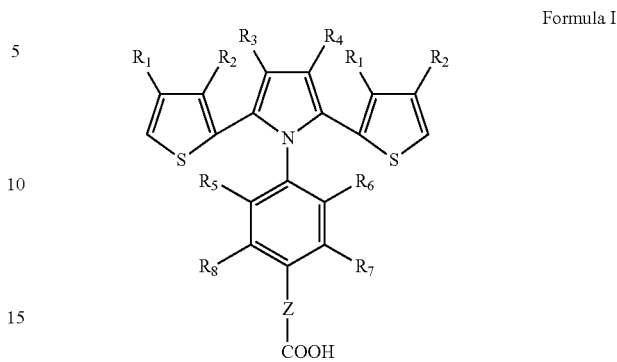

Formula I and processes for the preparation of the dithienylpyrrole compounds represented by Formula I. Also disclosed herein are compositions having one or more dithienylpyrrole polymers, wherein the dithienylpyrrole polymer include at least two of the monomer units represented by Formula Ia.

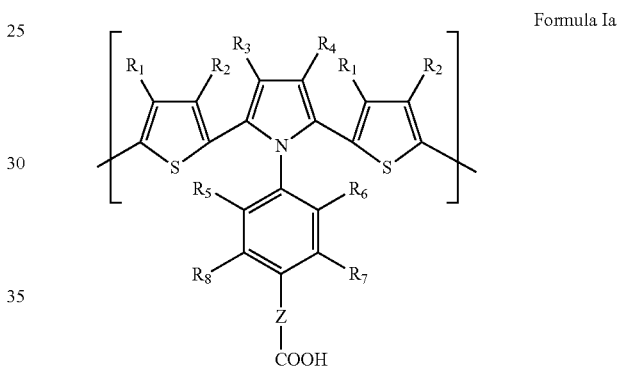

Formula Ia

In some embodiments, the compositions further comprise metal nanostructures.

Methods for the preparation of a nanostructure film on a surface of a substrate are also disclosed herein. Also disclosed are biosensors having a working electrode comprising one or more dithienylpyrrole polymers disclosed herein. The present disclosure also includes methods of using the biosensors.

Definitions

As used herein, "alkyl" refers to a straight or branched hydrocarbon chain that comprises a fully saturated (no double or triple bonds) hydrocarbon group. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and tert-butyl. Typical alkyl groups include, but are in no way limited to, methyl, ethyl, propyl, isopropyl, butyl, isobutyl, tertiary butyl, pentyl, hexyl, and the like. The alkyl group may be substituted or unsubstituted.

As used herein, "alkylene" refers to a straight or branched divalent hydrocarbon group. An alkylene group, for example, can have from 1 to 12 carbon atoms, more specifically 1 to about 10 carbon atoms. "$C_U$-$C_V$ alkylene" refers to alkylene groups having from U to V carbon atoms. Non-limiting examples of alkylene group include methylene, ethylene, propylene, butylene, pentylene, hexylene, heptylene, octylene, nonylene, and decylene.

As used herein, "alkylene" refers to an unsaturated straight or branched monovalent hydrocarbon group with one or more carbon-carbon double bonds. An alkylene group can, for example, have from 2 to 10 carbon atoms. "$C_U$-$C_V$ alkylene" refers to alkylene groups having from U to V carbon atoms.

As used herein, "alkyne" refers to an unsaturated straight or branched monovalent hydrocarbon group with one or more carbon-carbon triple bonds. An alkyne group can, for example, have from 2 to 10 carbon atoms. "$C_U$-$C_V$ alkyne" refers to alkyne groups having from U to V carbon atoms.

As used herein, "alkenylene" refers to a straight or branched divalent hydrocarbon group. An alkenylene group can, for example, have from 2 to 10 carbon atoms. "$C_U$-$C_V$ alkenylene" refers to alkenylene groups having from U to V carbon atoms.

As used herein, "alkynylene" refers to a straight or branched divalent hydrocarbon group. An alkynylene group can, for example, have from 2 to 10 carbon atoms. "$C_U$-$C_V$ alkynylene" refers to alkynylene groups having from U to V carbon atoms.

As used herein, "halogen" refers to fluoro, chloro, bromo and iodo.

As used herein, "working electrode" refers to an electrode at which one or more analyte is electrooxidized or electroreduced.

As used herein, "reference electrode" refers to an electrode has constant electrochemical potential.

As used herein, "auxiliary electrode" refers to an electrode used in a three electrode electrochemical cell for voltammetric analysis, which is used for transferring electric current to the working electrode.

As used herein, the "operating lifetime" of a working electrode in a sensor refers to the time interval between the conditioning of the working electrode and the moment when the electrochemical response of the sensor drops below 95% of its original response. Accordingly, the working electrode is considered to be unusable when its electrochemical response becomes lower than 95% of its original response.

As used herein, the term "bioreactive material" refers to an agent, material or composition that alone or when combined with another agent, material or composition and exposed to a test sample will form a chemical reaction and/or be altered in appearance or in another optical, chemically, physically, or electronically readable or detectable manner when a target analyte is present in the test sample.

Dithienylpyrrole Monomers and Methods of Making the Monomers

Some embodiments disclosed herein provide a dithienylpyrrole compound represented by Formula I:

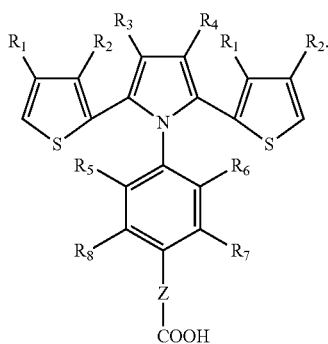

Formula I

In some embodiments, Z is a bivalent hydrocarbyl group selected from the group consisting of alkylene, alkenylene and alkynylene, $R_1$, $R_2$, $R_3$, and $R_4$ are each independently $C_1$-$C_6$ alkyl, $C_2$-$C_6$ alkylene, $C_2$-$C_6$ alkyne, hydrogen or halogen; and $R_5$, $R_6$, $R_7$, and $R_8$ are each independently $C_1$-$C_{10}$ alkyl, $C_2$-$C_{10}$ alkylene, $C_1$-$C_{10}$ alkyne, hydrogen, or halogen.

In some embodiments, Z is a bivalent hydrocarbyl group. Non-limiting examples of bivalent hydrocarbyl group include alkylene, alkenylene and alkynylene. For example, Z can be $C_1$-$C_{10}$ alkylene, $C_2$-$C_{10}$ alkenylene, or $C_2$-$C_{10}$ alkynylene. In some embodiments, Z is $C_1$-$C_{10}$ linear alkylene, $C_2$-$C_{10}$ linear alkenylene, or $C_2$-$C_8$ linear alkynylene. In some embodiments, Z is methyl, ethyl, or propyl.

In some embodiments, $R_1$, $R_2$, $R_3$, and $R_4$ are each independently $C_1$-$C_6$ alkyl, $C_2$-$C_6$ alkylene, $C_2$-$C_6$ alkyne, hydrogen or halogen. In some embodiments, $R_1$, $R_2$, $R_3$, $R_4$, $R_5$, $R_6$, $R_7$, and $R_8$ are each independently hydrogen. In some embodiments, $R_1$, $R_2$, $R_3$, $R_4$, $R_5$, $R_6$, $R_7$, and $R_8$ are each independently halogen.

In some embodiments, Z is alkylene, alkenylene or alkynylene; and $R_1$, $R_2$, $R_3$, $R_4$, $R_5$, $R_6$, $R_7$, and $R_8$ are each independently hydrogen.

Examples of the dithienylpyrrole compounds disclosed herein include, but not limited to, 2,5-di(2-thienyl)-1-pyrrol-1-(p-phenylacetic acid), 2,5-di(2-thienyl)-1-pyrrol-1-(p-phenylpropanoic acid, 2,5-di(2-thienyl)-1-pyrrol-1-(p-phenylpentanoic acid, 2,5-di(2-thienyl)-1-pyrrol-1-(p-phenylcaproic acid, or 2,5-di-(2-thienyl)-1H-pyrrole-1-(p-phenylbutanoic acid). In some embodiments, the dithienylpyrrole compound is 2,5-di(2-thienyl)-1-pyrrol-1-(p-phenylacetic acid) or 2,5-di-(2-thienyl)-1H-pyrrole-1-(p-phenylbutanoic acid).

A non-limiting process for the preparation of a compound represented by Formula I includes:

(1) contacting an optionally substituted thiophene

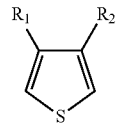

with a succinyl chloride

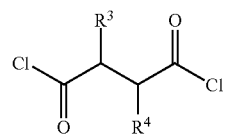

to obtain a first intermediate

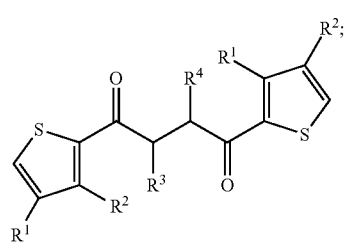

(2) contacting the first intermediate

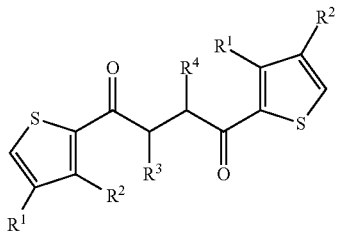

with a cyanoaniline

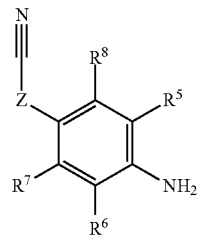

to obtain a second intermediate

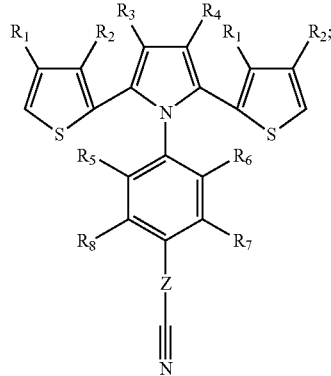

(3) hydrolyzing the nitrile group of the second intermediate to obtain the compound of Formula I

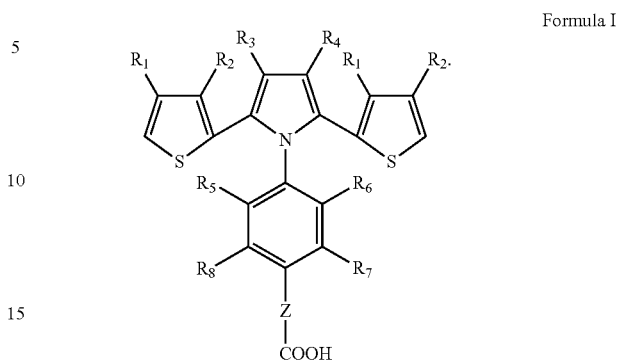

In some embodiments, Z is a bivalent hydrocarbyl group. Non-limiting examples of bivalent hydrocarbyl group include alkylene, alkenylene and alkynylene. For example, Z can be $C_1$-$C_{10}$ alkylene, $C_2$-$C_{10}$ alkenylene, or $C_2$-$C_{10}$ alkynylene. In some embodiments, Z is $C_1$-$C_{10}$ linear alkylene, $C_2$-$C_{10}$ linear alkenylene, or $C_2$-$C_8$ linear alkynylene. In some embodiments, Z is methyl, ethyl, or propyl.

In some embodiments, $R_1$, $R_2$, $R_3$, and $R_4$ are each independently $C_1$-$C_6$ alkyl, $C_2$-$C_6$ alkylene, $C_2$-$C_6$ alkyne, hydrogen or halogen. In some embodiments, $R_1$, $R_2$, $R_3$, $R_4$, $R_5$, $R_6$, $R_7$, and $R_8$ are each independently hydrogen. In some embodiments, $R_1$, $R_2$, $R_3$, $R_4$, $R_5$, $R_6$, $R_7$, and $R_8$ are each independently halogen.

In some embodiments, Z is alkylene, alkenylene or alkynylene; $R_1$, $R_2$, $R_3$, and $R_4$ are each independently $C_1$-$C_6$ alkyl, $C_2$-$C_6$ alkylene, $C_2$-$C_6$ alkyne, hydrogen or halogen; and $R_5$, $R_6$, $R_7$, and $R_8$ are each independently $C_1$-$C_{10}$ alkyl, $C_2$-$C_{10}$ alkylene, $C_1$-$C_{10}$ alkyne, hydrogen, or halogen.

In some embodiments, the optionally substituted thiophene

reacts with the optionally substituted succinyl chloride

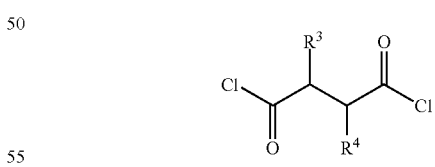

in the presence of aluminium trichloride. In some embodiments, the optionally substituted thiophene

reacts with the succinyl chloride

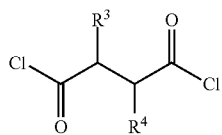

in the presence of at least one organic solvent. Examples of the organic solvent include, but not limited to, dichloromethane, n-hexane, n-heptane, carbon tetrachloride, and a mixture thereof.

In some embodiments, the first intermediate

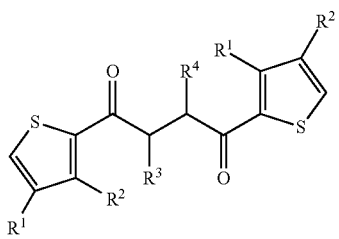

reacts with the cyanoaniline

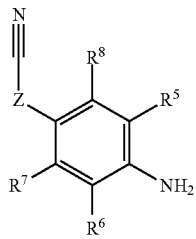

in the presence of an acid catalyst. The acid catalyst can be organic acid, inorganic acid, or a mixture thereof. Examples of the acid catalyst include, but not limited to, p-toluenesulfonic acid and naphthalene sulfonic acid.

In some embodiments, the compound of Formula I is obtained from the second intermediate

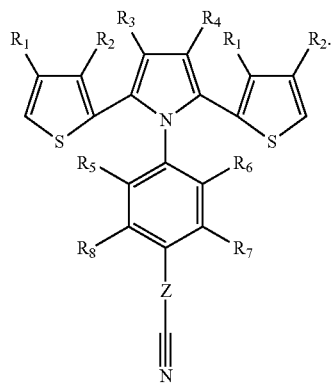

by alkaline hydrolysis. The alkaline hydrolysis can, for example, carried out in a mixture of potassium hydroxide aqueous solution and an organic solvent under reflux.

Compositions Including Dithienylpyrrole Polymers

Some embodiments disclosed herein include a composition having one or more dithienylpyrrole polymers. In some embodiments, the dithienylpyrrole polymer comprises at least two of the monomer units represented by Formula Ia:

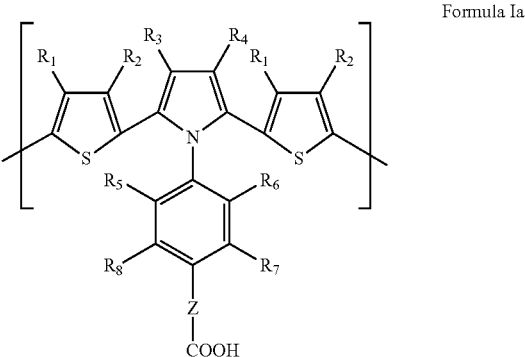

Formula Ia $Z$, $R_1$, $R_2$, $R_3$, $R_4$, $R_5$, $R_6$, $R_7$, and $R_8$ are as defined above.

The monomer unit can be, but not limited to, a 2,5-di(2-thienyl)-1-pyrrol-1-(p-phenylacetic acid) monomer, a 2,5-di (2-thienyl)-1-pyrrol-1-(p-phenylpropanoic acid monomer, a 2,5-di(2-thienyl)-1-pyrrol-1-(p-phenylpentanoic acid monomer, a 2,5-di(2-thienyl)-1-pyrrol-1-(p-phenylcaproic acid monomer, or a 2, 5-di-(2-thienyl)-1H-pyrrole-1-(p-phenylbutanoic acid) monomer. In some embodiments, the monomer unit is a 2,5-di(2-thienyl)-1-pyrrol-1-(p-phenylacetic acid) monomer or a 2,5-di-(2-thienyl)-1H-pyrrole-1-(p-phenylbutanoic acid) monomer In some embodiments, the composition further comprises one or more metal nanostructures. The types of the metal nanostructures are not particularly limited. For example, the metal nanostructures can be metal nanoparticles, metal nanowires, metal nanocube, metal nanorod, metal nanopyramid, metal nanotube, or a combination thereof. Examples of the metal nanostructures include, but are not limited to, gold nanostructures, silver nanostructures, palladium nanostructures, copper nanostructures, nickel nanostructures, platinum nanostructures, rhodium nanostructures, ruthenium nanostructures, and any combinations thereof. In some embodiments, the metal nanostructures comprise gold nanostructures. In some embodiments, the metal nanostructures comprise gold nanowires.

The total amount of the dithienylpyrrole polymer in the composition is not particularly limited and can vary depending upon the desired use. The total amount of the polymer in the composition can, for example, be at least about 1% by weight; at least about 2% by weight; at least about 5% by weight; at least about 10% by weight; at least about 15% by weight; at least about 20% by weight. The total amount of the polymer in the composition may, for example, be less than or equal to about 100% by weight, less than or equal to about 99% by weight; less than or equal to about 90% by weight; less than or equal to about 70% by weight; less than or equal to about 50% by weight; less than or equal to about 30% by weight; less than or equal to about 10% by weight; less than or equal to about 5% by weight, or less than or equal to about 1% by weight.

The total amount of the metal nanostructures in the composition is also not particularly limited and can vary depending upon the desired use. The total amount of the metal nanostructures in the composition can, for example, be at least about 1% by weight; at least about 2% by weight; at least about 5% by weight; at least about 10% by weight; at least about 15% by weight; at least about 20% by weight. The total amount of the metal nanostructures in the composition may, for example, be less than or equal to about 100% by weight, less than or equal to about 99% by weight; less than or equal to about 90% by weight; less than or equal to about 70% by weight; less than or equal to about 50% by weight; less than or equal to about 30% by weight; less than or equal to about 10% by weight; less than or equal to about 5% by weight, or less than or equal to about 1% by weight.

The weight ratio of the dithienylpyrrole polymer and the metal nanostructures in the composition can also vary. For example, the weight ratio of the dithienylpyrrole polymer and the metal nanostructures can be about 0.1:1, about 0.25:1, about 0.5:1, about 0.75:1, about 1:1, about 1.25:1, about 1.5:1, about 1.75:1, about 2:1, about 2.25:1, about 2.5:1, about 2.75:1, about 3:1, about 3.25:1, about 3.5:1, about 3.75:1, about 4:1, about 5:1, or about 6:1. In some embodiments, the weight ratio of the dithienylpyrrole polymer and the metal nanostructures is about 1:1 to about 3:1.

The composition can, in some embodiments, be in the form of a solid that includes one or more of the dithienylpyrrole polymers described herein. In some embodiments, a solid form of the composition can be obtained by precipitating or drying the composition from solution (e.g., solvent casting).

The compositions disclosed herein can be in various forms, including but not limited to, the form of a film, a membrane, a foil, or a combination thereof. In some embodiments, the composition forms a polymeric membrane.

Methods for Making Nanostructure Films

Some embodiments disclosed herein provide a method for the preparation of a nanostructure film on a surface of a substrate, wherein the nanostructure film includes one or more of the dithienylpyrrole polymers disclosed herein. The method can include, for example, forming a composition comprising dithienylpyrrole monomers, at least one metal precursor, at least one organic solvent, at least one supporting electrolyte, and at least one amine compound; allowing metal nanostructures to form in the composition; and contacting the composition with a substrate under a condition effective to covalently bound two or more dithienylpyrrole monomers to form a dithienylpyrrole polymer and forming the nanostructure film on at least a portion of a surface of the substrate.

In some embodiments, the dithienylpyrrole polymer comprises at least two of the monomer units represented by Formula Ia:

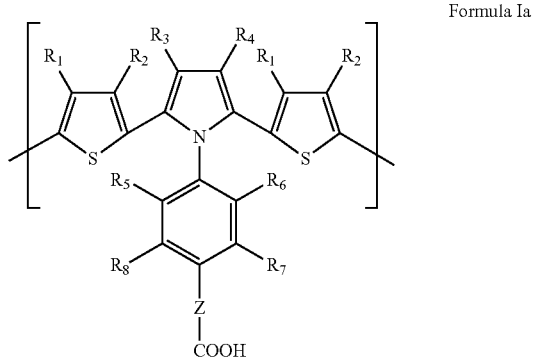

Formula Ia wherein Z, $R_1$, $R_2$, $R_3$, $R_4$, $R_5$, $R_6$, $R_7$, and $R_8$ are as defined above.

The percentages by weight of the dithienylpyrrole monomers, the metal precursor, the organic solvent, the supporting electrolyte, and the amine compound in the composition is not particularly limited and can vary depending upon desired use of the resulting nanostructure film. In some embodiments, the weight ratio of the dithienylpyrrole monomers, the metal precursor, the organic solvent, the supporting electrolyte, and the amine compound in the composition is about 1:1:83:10:5 to about 3:1:66:20:10. In weight percentages, the weight ratio would translate to the following: the percentage by weight of the dithienylpyrrole monomers in the composition is about 1 wt. % to about 3 wt. %, the percentage by weight of the metal precursor in the composition is about 1%, the percentage by weight of the organic solvent in the composition is about 66 wt. % to about 83 wt. %, the percentage by weight of the supporting electrolyte in the composition is about 10 wt. % to about 20 wt. %, and the percentage by weight of the amine compound in the composition is about 5 wt. % to about 10 wt. %. For example, the percentage by weight of the dithienylpyrrole monomers in the composition may be about 1 wt %, about 1.5 wt. %, about 2 wt. %, about 2.5 wt. %, about 3 wt. %, or a range between any two of these values; the percentage by weight of the metal precursor in the composition may be about 1%; the percentage by weight of the organic solvent in the composition may be about 66 wt. %, about 70 wt. %, about 75 wt. %, about 80 wt. %, about 83 wt % or a range between any two of these values; the percentage by weight of the supporting electrolyte in the composition may be about 10 wt. %, about 14 wt. %, about 16 wt. %, about 18 wt. %, about 20 wt. %, or a range between any two of these values; and the percentage by weight of the amine compound in the composition may be about 5 wt. %, about 6 wt. %, about 7 wt. %, about 8 wt. %, about 9 wt. %, about 10 wt. %, or a range between any two of these values.

The monomer unit can be, but not limited to, a 2,5-di(2-thienyl)-1-pyrrol-1-(p-phenylacetic acid) monomer, a 2,5-di(2-thienyl)-1-pyrrol-1-(p-phenylpropanoic acid monomer, a 2,5-di(2-thienyl)-1-pyrrol-1-(p-phenylpentanoic acid monomer, a 2,5-di(2-thienyl)-1-pyrrol-1-(p-phenylcaproic acid monomer, or a 2, 5-di-(2-thienyl)-1H-pyrrole-1-(p-phenylbutanoic acid) monomer. In some embodiments, the monomer unit is a 2,5-di(2-thienyl)-1-pyrrol-1-(p-phenylacetic acid) monomer or a 2,5-di-(2-thienyl)-1H-pyrrole-1-(p-phenylbutanoic acid) monomer.

The type of the metal precursor is not particularly limited and can vary depending upon the desired use of the nanostructure film. The metal precursor can be, but not limited to, gold metal precursors, silver gold precursors, palladium metal precursors, copper metal precursors, nickel metal precursors, platinum metal precursors, rhodium nanostructures, ruthenium nanostructures, or a combination thereof. In some embodiments, the at least one metal precursor is a gold metal precursor. In some embodiments, the at least one metal precursor is $HAuCl_4$, $AgNO_3$ or a combination thereof. In some embodiments, the metal nanostructures are nanoparticles, metal nanowires, metal nanocube, metal nanorod, metal nanopyramid, metal nanotube, or a combination thereof.

The organic solvent can be, for example, a non-polar solvent, a polar aprotic solvent, a polar protic solvent, or combinations thereof. In some embodiments, organic solvent includes a polar aprotic solvent. Non-limiting examples of organic solvent include n-hexane, chloroform, dichloromethane, n-heptane, carbon tetrachloride, and a mixture thereof. In some embodiments, the organic solvent is n-heptane, chloroform or dichloromethane.

In some embodiments, the at least one supporting electrolyte is a compound represented by Formula II: $(Y)_4N^-ClO4^-$, wherein Y is a $C_1$-$C_{30}$ alkyl, $C_1$-$C_{30}$ alkylene, $C_1$-$C_{30}$ alkyne, or an aromatic hydrocarbon group. For example, Y can be a $C_1$-$C_4$ linear alkyl. Examples of the supporting electrolyte include, but are not limited to, tetrabutylammonium perchlorate, tetrapropylammonium perchlorate, tetramethylammonium perchlorate, tetraamylammonium perchlorate, tetramethylammonium acetate, hexadecyltrimethylammonium acetate, hexadecyltrimethylammonium perchlorate, and a combination thereof. In some embodiments, the supporting electrolyte is tetrabutylammonium perchlorate or tetrapropylammonium perchlorate, In some embodiments, the at least one amine compound is a compound represented by Formula III:

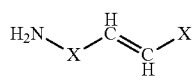

Formula III wherein X is a $C_6$-$C_{10}$ alkyl. Non-limiting examples of the amine compound include oleylamine, 7-tetradecenylamine, 8-hexadecenylamine, and 11-docosenylamine. In some embodiments, the at least one amine compound is oleylamine.

The steps and/or conditions for forming the composition are not particularly limited. Any suitable method of combining the ingredients is within the scope of the present disclosure. For example, the at least one amine compound can be first combined (mixed or dissolved) in the organic solvent with the at least one metal precursor to form a first mixture. Electrolyte and the dithienylpyrrole monomers can then be added to the first mixture to form the composition. The first mixture can be maintained at various temperatures to allow the reaction between the amine compound and the metal precursor, for example, about −20° C., about −10° C., about 0° C., about 10° C., about 15° C., about 20° C., about 25° C., about 30° C., about 35° C., about 40° C., about 45° C., about 50° C., about 55° C., about 60° C., about 65° C., about 70° C., about 75%, about 80° C., or a range between any two of these values. In some embodiments, the first mixture is maintained at about 45° C. to about 60° C. The time period that the first mixture is maintained can also vary, for example, about 1 hour, about 5 hours, about 10 hours, about 15 hours, about 20 hours, about 24 hours, about 30 hours, about 36 hours, about 42 hours, about 48 hours, about 54 hours, about 60 hours, about 66 hours, about 72 hours, or a range between any two of these values. In some embodiments, the first mixture is maintained for about 10 hours to about 48 hours.

The composition comprising the amine compound, the metal precursor, the organic solvent, the electrolyte and the dithienylpyrrole monomers can be stirred for about 1 hour, about 5 hours, about 10 hours, about 15 hours, about 20 hours, about 24 hours, about 30 hours, about 36 hours, about 42 hours, about 48 hours, about 54 hours, about 60 hours, about 66 hours, about 72 hours, or a range between any two of these values. The stirring can be carried out at various temperatures, for example, at about 10° C., about 15° C., about 20° C., about 25° C., about 30° C., about 35° C., about 40° C., about 45° C., about 50° C., about 55° C., about 60° C., about 65° C., about 70° C., about 75%, about 80° C., or a range between any two of these values. In some embodiments, the composition was stirred at a temperature of about 45° C. to about 60° C. for about 10 hours to about 48 hours.

The stirred composition can be maintained at various temperatures, for example, at about 10° C., about 15° C., about 20° C., about 25° C., about 30° C., about 35° C., about 40° C., about 45° C., about 50° C., about 55° C., about 60° C., or a range between any two of these values, to allow metal nanostructures to form in the composition. The time period that the stirred composition is maintained to allow metal nanostructures to form in the composition can also vary, for example, about 12 hours, about 18 hours, about 24 hours, about 30 hours, about 36 hours, about 42 hours, about 48 hours, about 54 hours, about 60 hours, about 66 hours, about 72 hours, about 78 hours, about 84 hours, or a range between any two of these values. In some embodiments, forming the composition further comprises maintaining the stirred composition at about room temperature for about 48 hours to about 72 hours.

In some embodiments, contacting the composition with the substrate comprises cyclic voltammetry scanning. The voltage at which the cyclic voltammetry scanning is performed can be, for example, about 0 V, about 0.1 V, about 0.2 V, about 0.3 V, about 0.4 V, about 0.5 V, about 0.6 V, about 0.7 V, about 0.8 V, about 0.9 V, about 1 V, about 1.25 V, about 1.5 V, about 1.75 V, about 2 V, or a range between any two of these values. In some embodiments, the cyclic voltammetry scanning is performed at a voltage of about 0 V to about 1 V. In some embodiments, the cyclic voltammetry scanning is performed at a voltage of about 0.2 V to about 0.6 V.

The scanning rate of the cyclic voltammetry scanning can also vary, for example, at about 10 mV/s, about 50 mV/s, about 100 mV/s, about 150 mV/s, about 200 mV/s, about 250 mV/s, about 300 mV/s, about 350 mV/s, about 400 mV/s, about 450 mV/s, about 500 mV/s, about 550 mV/s, about 600 mV/s, about 650 mV/s, about 700 mV/s, or a range between any two of these values. In some embodiments, the cyclic voltammetry scanning is performed at a scanning rate of about 10 mV/s to about 500 mV/s. In some embodiments, the cyclic voltammetry scanning is performed at a scanning rate of about 100 mV/s or 150 mV/s.

In some embodiments, the substrate is an electrode. As used herein the term "electrode" refers to a composition, which, when connected to an electronic device, is able to sense a current or charge and convert it to a signal. Examples of electrodes include, but are not limited to, metals and their oxides, for example gold, platinum, palladium, silicon aluminium; platinum oxide, titanium oxide, tin oxide, indium tin oxide, palladium oxide, silicon oxide, aluminium oxide, molybdenum oxide ($Mo_2O_6$), tungsten oxide ($WO_3$) and ruthenium oxides; and carbon (for example, glassy carbon electrodes, graphite and carbon paste). In some embodiments, the electrode is a glassy carbon electrode. In some embodiments, the electrode is a gold electrode.

Biosensor Comprising Nanostructure Films

Also disclosed herein are biosensors including nanostructure films. For example, the biosensor may comprise a working electrode configured to immobilize a bioreactive material, wherein the bioreactive material is reactive with a target material, wherein the working electrode comprises a dithienylpyrrole polymer and metal nanostructures, wherein the dithienylpyrrole polymer comprises at least two of the monomer units represented by Formula Ia:

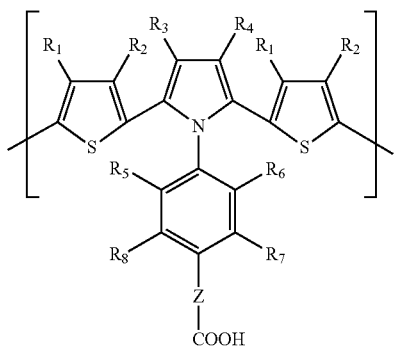

Formula Ia wherein Z, $R_1$, $R_2$, $R_3$, $R_4$, $R_5$, $R_6$, $R_7$, and $R_8$ are as defined above.

In some embodiments, the biosensor further comprises a reference electrode. Non-limiting examples of reference electrode include saturated calomel electrodes (SCE, $Hg/Hg_2Cl_2$), silver-silver chloride (Ag/AgCl) electrodes, and copper-copper(II) sulfate electrodes. In some embodiments, the reference electrode is an Ag/AgCl electrode.

In some embodiments, the biosensor further comprises an auxiliary electrode. In some embodiments, the auxiliary electrode is a platinum wire.

In some embodiments, the bioreactive material is reactive specifically with the target material. The types of the bioreactive material are not particularly limited. For example, the bioreactive material can be, but not limited to, enzymes, antibodies, nucleic acids, peptides, peptide nucleic acids (PNA), aptamers, and a combination thereof. In some embodiments, the bioreactive material is an enzyme, for example, glucose oxidase. In some embodiments, the bioreactive material is an antibody, for example, anti-aflatoxin $B_1$ antibody or anti-shrimp allergan antibody.

Non-limiting examples of metal nanostructures include gold nanostructures, silver nanostructures, palladium nanostructures, copper nanostructures, nickel nanostructures, platinum nanostructures, rhodium nanostructures, ruthenium nanostructures, and a combination thereof. In some embodiments, the metal nanostructures are in the form of metal nanoparticles, metal nanowires, metal nanocube, metal nanorod, metal nanopyramid, metal nanotube, or a combination thereof.

The operating lifetime of the working electrode can vary. For example, the working electrode can have an operating lifetime of about 1 week, about 2 weeks, about 3 weeks, about 4 weeks, about 5 weeks, about 6 weeks, about 7 weeks, about 8 weeks, about 3 months, about 6 months, about 9 months, about 12 months, about 15 months, about 16 months, about 18 months, or a range between any two of these values. In some embodiments, the polymeric sensing membrane can have an operating lifetime of more than about 4 weeks, more than about 6 weeks, more than about 9 weeks, more than about 12 weeks, more than about 15 weeks, more than about 18 weeks, or more than 20 weeks. In some embodiments, the working electrode has an operating lifetime of more than about 6 months. In some embodiments, the working electrode has an operating lifetime of more than about 12 months.

Methods for Detection Analytes in a Sample

Also disclosed herein are methods for detecting an analyte in a sample using a biosensor comprising the dithienylpyrrole polymers disclosed herein. The methods can, for example, include: providing a sample suspected of containing the analyte; contacting the sample with a biosensor, wherein the biosensor comprises a reference electrode and a working electrode configured to immobilize a bioreactive material, wherein the bioreactive material is reactive with the analyte, wherein the working electrode comprises a dithienylpyrrole polymer and metal nanostructures, wherein the dithienylpyrrole polymer comprises at least two of the monomer units represented by Formula Ia:

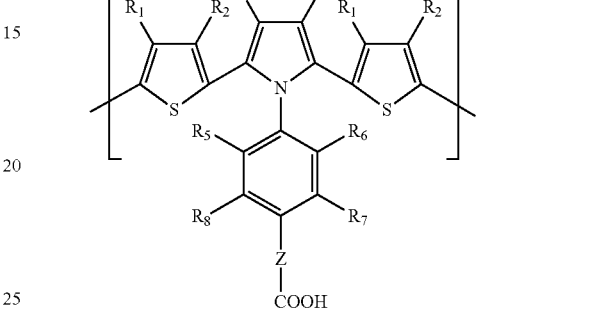

Formula Ia wherein Z, $R_1$, $R_2$, $R_3$, $R_4$, $R_5$, $R_6$, $R_7$, and $R_8$ are as defined above.

The bioreactive material can be reactive selectively or specifically with the analyte. For example, the bioreactive material can be, but not limited to enzymes, antibodies, nucleic acids, peptides, peptide nucleic acids (PNA), aptamers, or a combination thereof. In some embodiments, the bioreactive material is an enzyme or antibody. In some embodiments, the bioreactive material is immobilized onto the working electrode.

The analyte can be any biological or chemical entities. For example, the analyte can be, but not limited to, pesticides, small molecule compounds, macromolecules, polymers, biopolymers, polysaccharides, nucleic acids, proteins, hydrogen peroxide, antigens, bacteria, virus, ligand, pathogenic microorganisms, bacterial toxins, fungal toxins, viral toxins, and a combination thereof.

The concentration of the analyte in the sample can vary. For example, the concentration of the analyte in the sample can be about $10^{-18}$ mol/L (i.e., $10^{-18}$ M), $10^{-17}$ mol/L, $10^{-16}$ mol/L, $10^{-15}$ mol/L, $10^{-14}$ mol/L, $10^{-13}$ mol/L, $10^{-12}$ mol/L, $10^{-11}$ mol/L, about $10^{-10}$ M, about $10^{-9}$ M, about $10^{-8}$ M, about $10^{-7}$ M, about $10^{-6}$ M, about $10^{-5}$ M, about $10^{-4}$ M, about $10^{-3}$ M, about $10^{-2}$ M, about 0.1 M, and ranges between any two of these values. In some embodiments, the concentration of the analyte in the sample is about $10^{-3}$ mol/L to about $10^{-17}$ mol/L. In some embodiments, the concentration of the analyte in the sample is about $10^{-6}$ mol/L to about $10^{-17}$ mol/L. In some embodiments, the concentration of the analyte in the sample is not more than $10^{-9}$ mol/L.

Without being bound by theory, it will be appreciated that the dithienylpyrrole polymer compositions disclosed herein can allow stable bonding of bioreactive molecules to the biosensors, and thus retain reactivity of the bioreactive molecules. As the carboxyl group is linked to the aromatic ring in the monomer unit of formula Ia via a single covalent bond, it may avoid a decrease in chemical reactivity of the carboxyl group resulting from π-π conjugation between the carboxyl group and the aromatic ring of the monomer unit.

As a result, the dithienylpyrrole polymer compositions disclosed herein can easily form covalent bonds with the bioreactive molecules (such as enzymes, antibodies, DNA, and aptamers etc.). The dithienylpyrrole polymer compositions disclosed herein can be linked to bioreactive molecules through covalent bonding between the free carboxyl group of the polymer and the amino group of the bioreactive molecules, thereby improving the stability of the biosensor. Since the amino group of the bioreactive molecule is generally located deep within its spatial structure, the longer "connecting arm" of the dithienylpyrrole polymer can enable the bioreactive molecule to retain its original spatial configuration after being fixed onto the polymer.

In the methods for the preparation of the dithienylpyrrole polymer compositions as disclosed herein, organic amine compounds of formula III are used as chelating agent, template directing agent and reducing agent to gradually transform the metal precursor, such as chloroauric acid, to form metal nanostructures which can be dispersed in the organic solvent, thereby avoiding a direct redox reaction between the dithienylpyrrole monomer and the metal precursor which can deteriorate the dithienylpyrrole polymer that is formed and discourage attachment of the polymer to the biosensor.

The biosensors comprising the dithienylpyrrole polymer compositions as disclosed herein can be customized for a wide variety of applications. The specific application can be determined by the bioreactive material that is immobilized on the electrode. When the electrode is modified with different enzymes, it can be applied in rapid detection of residual chemicals (pesticides, veterinary drugs, hydrogen peroxide, etc.) in food. When the electrode is modified with different antibodies, it can be applied in rapid detection of mycotoxin and virus strains. When the electrode is modified with different DNA probes, it can be applied in rapid detection of pathogenic microorganism, mycotoxin and genetically modified food.

The electrochemical response sensitivity of the biosensors disclosed herein has been observed to be high as can be seen from the Examples. The biosensor has been used to detect the content of aflotoxin in food samples and the detection limit was observed to be about $10^{-15}$ mol/L. When used to detect shrimp allergen, the detection limit was observed to be about $10^{-10}$ mol/L.

The metal nanostructures in the dithienylpyrrole polymer compositions can form stable dispersions in the organic solvent. Therefore, the solutions used in the preparation process are stable and is unlikely to have unstable factors such as sedimentation during the modification of the electrode. Since the nanostructure film can be prepared by electrodeposition method, the electrochemical parameters such as temperature, voltage, time and current can be precisely controlled. These can result in uniform deposition of the dithienylpyrrole polymer compositions onto the electrode during each modification. The thickness of the film and the content of the metal nanostructures can be maintained for each batch, thereby ensuring consistent batch-to-batch reproducibility.

EXAMPLES

Additional embodiments are disclosed in further detail in the following examples, which are not in any way intended to limit the scope of the claims.

Example 1

Synthesis of Dithienylpyrrole Conducting Monomer

Step 1. Synthesis of 1,4-dithienylbutane-1,4-dione

Succinyl chloride was dissolved in dichloromethane, and anhydrous aluminium trichloride was added to the solution as the mixed solution is stirred. The mixed solution is cooled to about 0-5° C. Thiophene solution was slowly added dropwise into the cooled solution. The solution was continuously stirred for 5 hours, and poured into ice-cold water.

Concentrated hydrochloric acid was added to the solution and the organic phase was collected. The organic phase was washed with deionized water. The steps of washing with acid and water are repeated until no aluminium ions could be detected from the water phase. The organic phase was dried over anhydrous $MgSO_4$. The organic solvent was removed by reduced pressure distillation at room temperature. The obtained solid, 1,4-dithienylbutane-1,4-dione, was washed with anhydrous ethanol to remove the residual thiophene.

Step 2. Synthesis of 2,5-dithienyl-1-hydrocarbylcyanophenyl pyrrole

The 1,4-dithienylbutane-1,4-dione obtained from step 1 was dissolved in an organic solvent. A strong acid catalyst, for example p-toluenesulfonic acid or naphthalene sulfonic acid, and p-hydrocarbylcyanoaniline were added and the solution was refluxed under nitrogen protection for 24 hours. The solution was filtered and the filtrate was collected. The organic solvent in the filtrate was removed by reduced pressure distillation. The formed solid, 2,5-dithienyl-1-hydrocarbylcyanophenyl pyrrole, in the resulting filtrate was dissolved in dichloromethane and washed with water until it is neutral in pH. The organic phase was collected and the organic solvent is removed by reduced pressure distillation. The solid was recrystallized from dichloromethane.

Step 3. Synthesis of dithienylpyrrole conducting polymer monomer

The 2,5-dithienyl-1-hydrocarbylcyanophenyl pyrrole obtained from step 2 was dissolved in potassium hydroxide KOH solution. Ethoxyethyl ether was added to the solution and the resulting solution was refluxed for 6 hours. 6M of HCl and 2 M of $H_2SO_4$ were added to adjust the solution to acidic. The solution was cooled down, filtered, washed with water, and recrystallized from anhydrous ethanol to produce a dithienylpyrrole conducting polymer monomer as shown in Formula IV below, wherein R is alkyl, alkenyl, alkynyl or an aromatic hydrocarbon group.

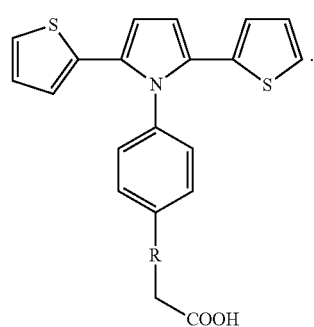

Formula IV

Example 2

Synthesis of 2,5-di(2-thienyl)-1-pyrrol-1-p-phenylacetic acid 5.5 mL of succinyl chloride, 16 g of anhydrous aluminium chloride and 100 mL of dichloromethane were added to a 250 mL round bottomed flask to form a mixed solution. The solution was cooled down to around 0° C. on an ice bath, and 9.6 mL of thiophene in n-hexane was added to the solution dropwise while stirring. Upon completion, the solution was continuously stirred at 18-20° C. for 4 hours and poured into ice-cold water. 5 mL of concentrated hydrochloric acid was slowly added dropwise and the solution was filtered, washed with 75 mL of saturated $NaHCO_3$ and dried under vacuum to produce 1,4-dithienylbutane-1,4-dione.

1.25 g of 1,4-dithienylbutane-1,4-dione was added into a 100 mL three-necked flask. 0.66 g of p-aminophenylacetonitrile, 1.03 g of p-toluenesulfonic acid and 15 mL of toluene were added to the flask and the solution was refluxed for 0.5 hour under nitrogen protection. The solution was filtered and the filtrate was collected. Toluene in the filtrate was removed by reduced pressure distillation. The resulting solids from the filtrate were dissolved in dichloromethane and washed with water until neutral in pH. The organic phase was collected and the dichloromethane was removed by reduced pressure distillation. The dissolved solids were recrystallized from the dichloromethane to give 2,5-dithienyl-1-pyrrol-1-p-phenylacetonitrile as a white solid.

2.73 g of 2,5-dithienyl-1-pyrrol-1-p-phenylacetonitrile, 1.0 g of KOH and 30 mL of ethoxyethanol-water (v/v=5:1) were added to a 250 mL three-necked flask, and the solution was heated to reflux for 5 hours and acidified with concentrated hydrochloric acid to pH 3. The heated solution was cooled, filtered and recrystallized from dichloromethane to give 2,5-di(2-thienyl)-1-pyrrol-1-p-phenylacetic acid as a yellow acicular crystal. Infra-red (IR) analysis (KBr) of the obtained 2,5-di(2-thienyl)-1-pyrrol-1-p-phenylacetic acid was 3430-3190 $cm^{-1}$ (OH), 1660 $cm^{-1}$ (C=O), 1510 $cm^{-1}$, 1417 $cm^{-1}$ (C—S).

Example 3

Preparation of an Electrode Based on poly[2,5-di-(2-thienyl)-1H-pyrrole-1-(p-phenylacetic acid)]

5 mL of n-hexane, 4 mg of chloroauric acid and 200 mg of oleylamine were added to a 20 mL electrolytic cell, and magnetically stirred for 1 hour. 200 mg of tetrabutylammonium perchlorate and 2 mg of 2,5-di-(2-thienyl)-1H-pyrrole-1-(p-phenylacetic acid) were added to the electrolytic cell and stirred well. The mixture was reacted at 55° C. for 10 hours, and was placed at room temperature for 72 hours to produce an electrolyte solution.

A glassy carbon electrode ($\varphi=2$ mm) was dipped into the electrolyte solution and was deposited with a functional conducting polymer/nanostructure network composite film at an electrochemical workstation. The electrochemical parameters used were: Voltage scanning range: 0~1V; Scanning rate: 100 mV/s. After 4 scans by cyclic voltammetry, the electrode was removed, washed with anhydrous ethanol and deionized water respectively, and then dried.

Example 4

Detection of Glucose by a Biosensor Based on poly[2,5-di-(2-thienyl)-1H-pyrrole-1-(p-phenylacetic acid)]

The modified electrode prepared according to the general procedure described in Example 4 was activated in 20 mM 1-ethyl-3-[3-dimethylaminopropyl]carbodiimide hydrochloride (EDC)/N-hydroxysuccinimide (NHS) solution for 4 hours and was immersed in 10 mg/mL glucose oxidase solution for 24 hours to prepare a glucose biosensor.

The glucose biosensor was tested for the analysis performance at the electrochemical workstation. When the concentration of glucose is between $5\times10^{-6}$ and $8\times10^{-4}$ mol/L, the change of the peak current of the differential pulse voltammetric curve showed a linear relationship with the concentration of glucose. It was found that the detection limit was 1.2 µM and the glucose sensor retained more than 95% of its electrochemical response after being placed at 4° C. for 4 weeks. The glucose biosensor was successfully used to determine trace glucose in serum with a spike recovery rate of between 95.2% and 101.7%.

Example 5

Preparation of an Electrode Based on poly[2,5-di-(2-thienyl)-1H-pyrrole-1-(p-phenylbutanoic acid)]

5 mL of chloroform, 5 mg of chloroauric acid and 180 mg of oleylamine were successively added to a 20 mL electrolytic cell and magnetically stirred for 1 hour. 200 mg of tetrapropylammonium perchlorate and 2 mg of 2,5-di-(2-thienyl)-1H-pyrrole-1-(p-phenylbutanoic acid were added to the electrolytic cell and reacted at 50° C. for 16 hours. The reaction mixture was placed at room temperature for 48 hours to produce an electrolyte solution.

A gold electrode ($\varphi=2$ mm) was dipped into the electrolyte solution and was deposited with a functional conducting polymer/gold nanowires network composite film at the electrochemical workstation. The electrochemical parameters used were: Voltage scanning range: 0~1V, Scanning rate: 50 mV/s. After 6 scans by cyclic voltammetry, the electrode was removed, washed with anhydrous ethanol and deionized water sequentially, and then dried.

Example 6

Detection of aflatoxin $B_1$ by a Biosensor Based on poly[2,5-di-(2-thienyl)-1H-pyrrole-1-(p-phenylbutanoic acid)]

Aflatoxin $B_1$ was added into 20 mL of PBS (pH 7) to prepare phosphate buffers containing aflatoxin $B_1$ at various concentrations.

The modified electrode prepared according to the general procedure described in Example 5 was activated with 20 mM EDC/NHS solution for 4 hours, and immersed in 1 mg/mL anti-aflatoxin $B_1$ antibody solution for 24 hours. The electrode was placed in PBS (pH 7) containing 5 mg/mL BSA to block the remaining active sites of the antibody for 4 hours. The electrode was removed, washed with PBS (pH 7), and dried to produce an aflatoxin $B_1$ biosensor. The aflatoxin $B_1$ biosensor was dipped into the buffers solutions. The solutions were magnetically stirred at 100 rpm at 37° C. for 20 minutes. The electrode was then washed with deionized water and dried with nitrogen gas for future use.

A three-electrode system was used. In the three-electrode system, the aflatoxin $B_1$ biosensor was used as working electrode, Ag/AgCl standard electrode was used as reference electrode, and platinum wire was used as auxiliary electrode. Using 0.01 mol/L phosphate buffer (pH 7.0) containing $1\times10^{-3}$ mol/L $Fe(CN)_6^{3-/4-}$ as testing solution, cyclic voltammetry (Voltage: −0.2~0.6 V, scanning rate: 100 mV/s) and AC impedance (Frequency: $1\sim10^5$ Hz, AC perturbation signal amplitude: 5 mV, DC bias voltage: 0.3 V) were used to analyze the electrochemistry and the analysis performance of the biosensor. When the concentration of aflatoxin $B_1$ was in the range of $5\times10^{-15} \sim 3\times10^{-13}$ mol/L, the AC impedance of the biosensor had a linear relationship with the concentration, with a correlation coefficient $R^2$ of 0.994, and a detection limit of $1.6\times10^{-15}$ mol/L.

It was found that the biosensor's electrochemical response remained almost unchanged after stored at 4° C. for over 20 weeks. The aflatoxin $B_1$ biosensor was successfully used to determine the content of trace aflatoxin $B_1$ in food and the result is consistent with that of HPLC analysis.

Example 7

Preparation of an Electrode Based on poly[2,5-di-(2-thienyl)-1H-pyrrole-1-(p-phenylacetic acid)]

5 mL of dichloromethane, 6 mg of chloroauric acid and 190 mg of oleylamine were added to a 20 mL electrolytic cell, and magnetically stirred for 1 hour. 200 mg of tetrabutylammonium perchlorate and 2 mg of 2,5-di-(2-thienyl)-1H-pyrrole-1-(p-phenylacetic acid) were added to the electrolytic cell to form a mixture. The mixture was first reacted at 55° C. for 12 hours, and then placed at room temperature for 48 hours to produce an electrolyte solution.

A glassy carbon electrode ($\varphi=2$ mm) was dipped into the electrolyte solution. A three-electrode system was used, in which a glassy carbon electrode, a platinum electrode and an Ag/AgCl standard electrode were used as working electrode, auxiliary electrode and reference electrode, respectively. Cyclic voltammetric potential scanning was performed by controlling the voltage range in the range of 0~1V and the scanning rate at 150 mV/s. After 4 scans by cyclic voltammetry, the electrodes were removed, washed with anhydrous ethanol and deionized water successively, and dried to produce modified electrodes with functional conducting polymer/gold nanostructures network composite film.

Example 8

Detection of Anti-Shrimp Allergen by a Biosensor Based on poly[2,5-di-(2-thienyl)-1H-pyrrole-1-(p-phenylbutanoic acid)]

The modified electrode prepared according to the general procedure described in Example 7 was activated in 20 mM EDC/NHS solution for 4 hours, and was immersed in 10 mg/mL anti-shrimp allergen antibody solution for 24 hours. The electrode was placed in PBS (pH 7) containing 5 mg/mL BSA to block the remaining active sites of the antibody for 4 hours. The electrode was removed, washed with a buffer and dried to prepare an anti-shrimp allergen biosensor.

Various amounts of shrimp allergen were added to 20 mL of PBS (pH 7) respectively to prepare sample solutions containing shrimp allergen at different concentrations. The anti-shrimp allergen biosensor was dipped into the samples solutions, and the solutions were magnetically stirred at 100 rpm at 37° C. for 20 minutes. The electrode was washed with water and dried with nitrogen gas for future use.

A three-electrode system was used, in which the antibody-antigen complex electrode was used as working electrode, Ag/AgCl standard electrode as reference electrode, and platinum wire as auxiliary electrode. 0.01 mol/L phosphate buffer (pH 7.0) containing $1\times10^{-3}$ mol/L $Fe(CN)_6^{3-/4-}$ was used as testing solution, and differential pulse voltammetry was used to test the analysis performance of the biosensor. When the concentration of the shrimp allergen was in the range of $1\times10^{-10} \sim 1\times10^{-8}$ ng/mL, the change of the peak current of the differential pulse voltammetry of the biosensor showed a linear relationship with the concentration of the shrimp allergen, with a correlation coefficient $R^2$ of 0.9998, and a detection limit of $1.8\times10^{-10}$ ng/mL. After the biosensor was stored at 4° C. for over 20 weeks, its electrochemical response remained almost unchanged. This biosensor was successfully used to determine the content of trace shrimp allergen in food samples. Its spike recovery rate was in the range of 96.8% to 107.1%.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method to prepare a nanostructure film on a surface of a substrate, the method comprising:
    forming a composition comprising dithienylpyrrole monomers, at least one metal precursor, at least one organic solvent, at least one supporting electrolyte, and at least one amine compound;
    allowing metal nanostructures to form in the composition;
    contacting the composition having the metal nanostructures with the substrate under a condition effective to covalently bind two or more dithienylpyrrole monomers to form a dithienylpyrrole polymer; and
    forming the nanostructure film on at least a portion of the surface of the substrate.

2. The method of claim 1, wherein forming the composition comprising the dithienylpyrrole monomers, the at least one metal precursor, the at least one organic solvent, the at least one supporting electrolyte, and the at least one amine compound comprises contacting the dithienylpyrrole monomers, the at least one metal precursor, the at least one organic solvent, the at least one supporting electrolyte, and the at least one amine compound in a weight ratio of about 1:1:83:10:5 to about 3:1:66:20:10.

3. The method of claim 1, wherein forming the composition comprising the dithienylpyrrole monomers, the at least one metal precursor, the at least one organic solvent, the at least one supporting electrolyte, and the at least one amine compound comprises contacting the dithienylpyrrole monomers represented by Formula Ia:

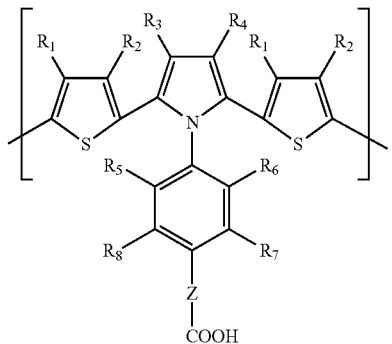

Formula Ia wherein:
Z is a bivalent hydrocarbyl group selected from the group consisting of alkylene, alkenylene, and alkynylene;
$R_1$, $R_2$, $R_3$, and $R_4$ are each independently $C_1$-$C_6$ alkyl, $C_2$-$C_6$ alkylene, $C_2$-$C_6$ alkyne, hydrogen, or halogen; and
$R_5$, $R_6$, $R_7$, and $R_8$ are each independently $C_1$-$C_{10}$ alkyl, $C_2$-$C_{10}$ alkylene, $C_1$-$C_{10}$ alkyne, hydrogen, or halogen, with the at least one metal precursor, the at least one organic solvent, the at least one supporting electrolyte, and the at least one amine compound.

4. The method of claim 3, wherein the dithienylpyrrole monomer is a 2,5-di(2-thienyl)-1-pyrrol-1-(p-phenylacetic acid) monomer or a 2,5-di-(2-thienyl)-1H-pyrrole-1-(p-phenylbutanoic acid) monomer.

5. The method of claim 1, wherein forming the composition comprising the dithienylpyrrole monomers, the at least one metal precursor, the at least one organic solvent, the at least one supporting electrolyte, and the at least one amine compound comprises contacting the dithienylpyrrole monomers, the at least one organic solvent, the at least one supporting electrolyte, and the at least one amine compound with the at least one metal precursor selected from the group consisting of gold metal precursors, silver gold precursors, palladium metal precursors, copper metal precursors, nickel metal precursors, platinum metal precursors, rhodium nanostructures, ruthenium nanostructures, and a combination thereof.

6. The method of claim 1, wherein forming the composition comprising the dithienylpyrrole monomers, the at least one metal precursor, the at least one organic solvent, the at least one supporting electrolyte, and the at least one amine compound comprises contacting the dithienylpyrrole monomers, the at least one metal precursor, the at least one supporting electrolyte, and the at least one amine compound with the at least one organic solvent selected from the group consisting of n-hexane, chloroform, dichloromethane, n-heptane, carbon tetrachloride, and a mixture thereof.

7. The method of claim 1, wherein forming the composition comprising the dithienylpyrrole monomers, the at least one metal precursor, the at least one organic solvent, the at least one supporting electrolyte, and the at least one amine compound comprises contacting the dithienylpyrrole monomers, the at least one metal precursor, the at least one organic solvent, and the at least one amine compound with the at least one supporting electrolyte represented by Formula II: $(Y)_4N^+ClO_4^-$, wherein Y is a $C_1$-$C_{30}$ alkyl, a $C_1$-$C_{30}$ alkylene, a $C_1$-$C_{30}$ alkyne, or an aromatic hydrocarbon group.

8. The method of claim 1, wherein forming the composition comprising the dithienylpyrrole monomers, the at least one metal precursor, the at least one organic solvent, the at least one supporting electrolyte, and the at least one amine compound comprises contacting the dithienylpyrrole monomers, the at least one metal precursor, the at least one organic solvent, and the at least one supporting electrolyte with the at least one amine compound represented by Formula III:

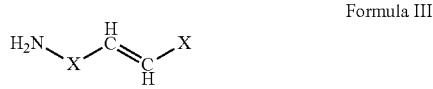

Formula III wherein X is a $C_6$-$C_{10}$ alkyl.

9. The method of claim 1, wherein contacting the composition having the metal nanostructures with the substrate comprises contacting the composition with an electrode.

10. The method of claim 1, wherein contacting the composition having the metal nanostructures with the substrate comprises cyclic voltammetry scanning.

11. A biosensor, comprising:
a working electrode configured to immobilize a bioreactive material, wherein the bioreactive material is reactive with a target material, and wherein the working electrode comprises the nanostructure film prepared according to claim 1.

12. The biosensor of claim 11, wherein the biosensor further comprises a reference electrode.

13. The biosensor of claim 11, wherein the bioreactive material is reactive specifically with the target material.

14. The biosensor of claim 11, wherein the bioreactive material is selected from the group consisting of enzymes, antibodies, nucleic acids, peptides, peptide nucleic acids (PNA), aptamers, and a combination thereof.

15. The method of claim 5, wherein the at least one metal precursor is a gold metal precursor, $HAuCl_4$, $AgNO_3$, or a combination thereof.

16. The method of claim 7, wherein Y is a $C_1$-$C_4$ linear alkyl.

17. The method of claim 7, wherein the at least one supporting electrolyte is selected from the group consisting of tetrabutylammonium perchlorate, tetrapropylammonium perchlorate, tetramethylammonium perchlorate, tetraamylammonium perchlorate, tetramethylammonium acetate, hexadecyltrimethylammonium acetate, hexadecyltrimethylammonium perchlorate, and a combination thereof.

18. The method of claim 8, wherein the at least one amine compound is selected from the group consisting of oleylamine, 7-tetradecenylamine, 8-hexadecenylamine, and 11-docosenylamine.

19. The method of claim 1, wherein forming the composition comprises stirring the composition at a temperature of about 45° C. to about 60° C. for about 10 hours to about 48 hours.

20. The method of claim 19, wherein forming the composition further comprises maintaining the stirred composition at about room temperature for about 48 hours to about 72 hours.

21. The method of claim 10, wherein the cyclic voltammetry scanning is performed at a voltage of about 0 V to about 1 V.

22. The method of claim 10, wherein the cyclic voltammetry scanning is performed at a scanning rate of about 10 mV/s to about 500 mV/s.

* * * * *

UNITED STATES PATENT AND TRADEMARK OFFICE
CERTIFICATE OF CORRECTION

PATENT NO. : 9,891,184 B2
APPLICATION NO. : 14/758421
DATED : February 13, 2018
INVENTOR(S) : Li et al.

It is certified that error appears in the above-identified patent and that said Letters Patent is hereby corrected as shown below:

In the Specification

In Column 1, Lines 5-6, delete "CROSS-REFERENCE TO RELATED APPLICATIONS" and insert -- CROSS-REFERENCE TO RELATED APPLICATION --, therefor.

In Column 1, Line 12, delete "filed December 31, 2012." and insert -- filed on December 31, 2012. --, therefor.

In Column 2, Line 61, delete "pyrrole-1-" and insert -- pyrrol-1- --, therefor.

In Column 3, Line 12, delete "thereof" and insert -- thereof. --, therefor.

In Column 4, Lines 23-24, delete "$(Y)_4N^-ClO4^{31}$," and insert -- $(Y)_4N^+ClO4^-$, --, therefor.

In Column 6, Line 23, delete "thereof" and insert -- thereof. --, therefor.

In Column 9, Line 64, delete "hereincan" and insert -- herein, can --, therefor.

In Column 10, Line 22, delete "polymer include" and insert -- polymer includes --, therefor.

In Column 15, Lines 49-54, delete " 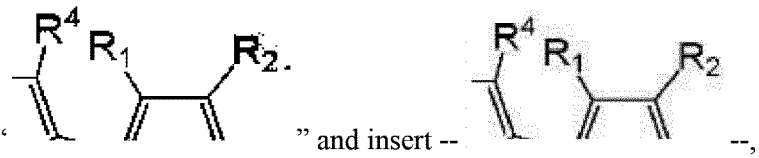 " and insert -- --, therefor.

In Column 16, Line 33, delete "monomer" and insert -- monomer. --, therefor.

In Column 18, Line 23, delete "1 wt %," and insert -- 1 wt. %, --, therefor.

Signed and Sealed this
Twenty-fourth Day of July, 2018

Andrei Iancu
*Director of the United States Patent and Trademark Office*

CERTIFICATE OF CORRECTION (continued)
U.S. Pat. No. 9,891,184 B2

In Column 18, Line 29, delete "83 wt %," and insert -- 83 wt. %, --, therefor.

In Column 19, Lines 4-5, delete "$(Y)_4N^-ClO4^-$," and insert -- $(Y)_4N^+ClO4^-$, --, therefor.

In Column 19, Lines 15, delete "perchlorate," and insert -- perchlorate. --, therefor.

In Column 23, Line 43, delete "aflotoxin" and insert -- aflatoxin --, therefor.

In Column 28, Line 43, delete "recitation no" and insert -- recitation, no --, therefor.

In Column 28, Line 65, delete "general such" and insert -- general, such --, therefor.

In Column 29, Line 5, delete "general such" and insert -- general, such --, therefor.